(12) United States Patent
Alvino

(10) Patent No.: US 9,072,580 B2
(45) Date of Patent: Jul. 7, 2015

(54) COMBINATION EYE CUP AND DROP DISPENSER

(76) Inventor: Joseph Alvino, Laguna Woods, CA (US)

(*) Notice: Subject to any disclaimer, the term of this patent is extended or adjusted under 35 U.S.C. 154(b) by 1710 days.

(21) Appl. No.: 12/151,604

(22) Filed: May 7, 2008

(65) Prior Publication Data
US 2009/0281508 A1 Nov. 12, 2009

(51) Int. Cl.
A61F 9/00 (2006.01)
A61H 35/02 (2006.01)

(52) U.S. Cl.
CPC .............. *A61F 9/0026* (2013.01); *A61H 35/02* (2013.01)

(58) Field of Classification Search
CPC ...... A61F 9/0026; A61H 35/02; A61M 35/00
USPC ............................ 604/301–302; 222/520, 549
See application file for complete search history.

(56) References Cited

U.S. PATENT DOCUMENTS

| | | | |
|---|---|---|---|
| 1,767,080 A * | 6/1930 | King .............................. | 604/301 |
| 1,900,201 A | 3/1933 | Sager | |
| 2,080,268 A * | 5/1937 | Harris ........................... | 604/298 |
| 2,343,610 A | 3/1944 | Apfelbaum ................... | 222/421 |
| 2,626,606 A * | 1/1953 | Campbell ..................... | 604/301 |
| 2,665,826 A * | 1/1954 | Mahoney ...................... | 222/422 |
| 2,754,821 A * | 7/1956 | Burbig et al. ................. | 604/298 |
| 2,815,156 A * | 12/1957 | Moy .............................. | 222/520 |
| 2,920,624 A * | 1/1960 | Lerner et al. .................. | 604/301 |
| 3,016,898 A * | 1/1962 | Erwin ........................... | 604/298 |
| 3,279,466 A * | 10/1966 | Mings ........................... | 604/302 |
| 3,945,381 A | 3/1976 | Silver ............................ | 128/249 |
| 4,111,200 A | 9/1978 | Sbarra et al. ................. | 128/233 |
| 4,629,456 A * | 12/1986 | Edwards ....................... | 604/300 |
| 4,733,802 A * | 3/1988 | Sheldon ....................... | 604/302 |
| 4,754,899 A * | 7/1988 | Stull ............................. | 222/521 |
| 4,834,728 A | 5/1989 | McKenna .................... | 604/301 |
| 4,960,407 A * | 10/1990 | Cope ............................ | 604/300 |
| 4,981,479 A * | 1/1991 | Py ................................ | 604/302 |
| 5,007,905 A * | 4/1991 | Bauer ........................... | 604/295 |
| 5,037,406 A * | 8/1991 | Smith et al. .................. | 604/301 |
| 5,090,598 A * | 2/1992 | Stull ........................ | 222/153.14 |
| 5,133,702 A | 7/1992 | Py ................................ | 604/302 |
| 5,178,613 A * | 1/1993 | Gibilisco ..................... | 604/294 |
| 5,181,632 A * | 1/1993 | Latter ...................... | 222/153.06 |
| 5,181,634 A * | 1/1993 | Gibilisco ..................... | 222/212 |
| 5,387,202 A | 2/1995 | Baron .......................... | 604/300 |
| 5,501,377 A * | 3/1996 | Dubach ........................ | 222/521 |
| 5,578,021 A | 11/1996 | Cornish ....................... | 604/300 |
| 6,033,389 A | 3/2000 | Cornish ....................... | 604/300 |
| 6,168,581 B1 * | 1/2001 | Buehler ........................ | 604/295 |
| 6,508,793 B1 * | 1/2003 | Harrold ........................ | 604/302 |
| 6,540,726 B1 * | 4/2003 | Follman et al. .............. | 604/294 |
| 2005/0211734 A1 * | 9/2005 | Spada et al. .................. | 222/420 |
| 2006/0079851 A1 * | 4/2006 | Guerrieri ..................... | 604/295 |
| 2006/0129113 A1 * | 6/2006 | Merrick ....................... | 604/294 |
| 2006/0253089 A1 * | 11/2006 | Lin ............................... | 604/301 |
| 2006/0282049 A1 * | 12/2006 | Lee .............................. | 604/300 |

(Continued)

*Primary Examiner* — Melanie Hand
*Assistant Examiner* — Paula L Craig
(74) *Attorney, Agent, or Firm* — Steins & Associates, P.C.

(57) ABSTRACT

A Combination Eye Cup and Drop Dispenser is disclosed. The dispenser has a nozzle within an eye cup so that the user's hand will be steadied by resting the eye cup over the eye. The eye cup is integrated with a cap that regulates the opening and closing of the dispenser bottle so that turning the eye cup will open or close the dispenser nozzle. The bottle neck has external threads configured to engage internal threads on the eye cup/cap.

14 Claims, 4 Drawing Sheets

(56) References Cited

U.S. PATENT DOCUMENTS

2007/0149932 A1* 6/2007 Nick .......................... 604/295
2007/0233021 A1* 10/2007 Poisson et al. ................ 604/295
2008/0208148 A1* 8/2008 Soon et al. ................... 604/301

* cited by examiner

COMBINATION EYE CUP AND DROP DISPENSER

BACKGROUND OF THE INVENTION

1. Field of the Invention

This invention relates generally to dispensers for eye medication and, more specifically, to a Combination Eye Cup and Drop Dispenser.

2. Description of Related Art

Administering eye drops to one's own eyes can be a simple, painless process for many people. For others, however, eye sensitivity, hand unsteadiness, or just simple inexperience can cause the user to have great difficulty actually getting the drops into the eye. Even experts at placing eye drops can miss the eye (or dispense a drop while the eye is momentarily closed), which often will result in the drop ending up elsewhere on the user's face or body. A conventional dispenser is depicted in FIGS. 1 and 2.

FIGS. 1 and 2 are perspective views of the conventional disposable eyedrop dispenser 10. The device 10 has a unitary bottle (or body) 12 and a nozzle 16 either formed thereon or attached thereto. The base of the nozzle 16 has external threads 18 formed thereon in order to engage internal threads (not shown) formed within the cap 14. This allows the cap 14 to be secured over the nozzle 16 when the dropper 10 is not in use.

The nozzle 16 has a tapered shape terminating in an orifice 20 at its end. To administer drops, the user must hold the uncapped dispenser 10 upside down with the nozzle 16 just separated from and above an eye. Squeezing the bottle 12 will then dispense individual drops (ideally) into the eye.

The problem with this prior design is that there is nothing to assist the user in stabilizing the dispenser 10 so that drops dispensed through the orifice 20 will land in the eye.

Numerous attempts have been made to solve this problem; examples of these devices are: Silver, U.S. Pat. No. 3,945,381 and Sbarra et al., U.S. Pat. No. 4,111,200. The Silver device is an "Eye Drop Dispenser and Cup." As its name suggests, the Silver device is a eye drop dispenser bottle that has an eye cup sheathing its nozzle. The cup allows the user to steady the tip of the nozzle over one's eye while the drops are dispensed. The Silver cup should minimize the propensity to miss the eye with the drops. The problem with Silver is that the nozzle is inconvenient to open and close. The user must remove the plug (element 22) in order to use the dropper.

Sbarra seeks to solve the cap problem. The Sbarra device is an improvement upon the Silver device in that there is a valve integrated into the dispenser. The Sbarra device requires the user to first twist the eye cup/bottle cap to a predetermined orientation, then upend the bottle over the eye, and then depress a button near the neck of the bottle in order to dispense a certain number of drops from the nozzle.

While the Sbarra device does eliminate the need for removal of the cap to dispense, it adds such complexity that it would tend to be cost-prohibitive to manufacture.

The concept for the present invention builds upon the inventor's six-year-long experiences attempting to properly self-administer as many as ten eye drops daily following cataract surgery. While only approximately five percent or fewer individuals experience post-surgical difficulties, the numbers can expect to increase as the average age of our population grows. The present invention is particularly useful for persons having additional obstacles to drop placement, such as living alone, having poor vision or poor balance, experiencing Parkinson's disease, suffering rotator cuff pain and/or osteoporosis of the elbow, neck, back or shoulder. Furthermore, poor depth perception can actually make the process dangerous for the user.

What is needed is a simplified eye drop dispenser and cup combination that is simple to manufacture and operate, and that does not require a separate cap to secure the contents.

SUMMARY OF THE INVENTION

In light of the aforementioned problems associated with the prior devices, it is an object of the present invention to provide a Combination Eye Cup and Drop Dispenser. The dispenser should have a nozzle within an eye cup so that the user's hand will be steadied by resting the eye cup over the eye. The eye cup should be integrated with a cap that regulates the opening and closing of the dispenser bottle so that turning the eye cup will open or close the dispenser nozzle. The bottle neck should have external threads configured to engage internal threads on the eye cup/cap.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a Combination Eye Cup and Drop Dispenser.

Figure 2:
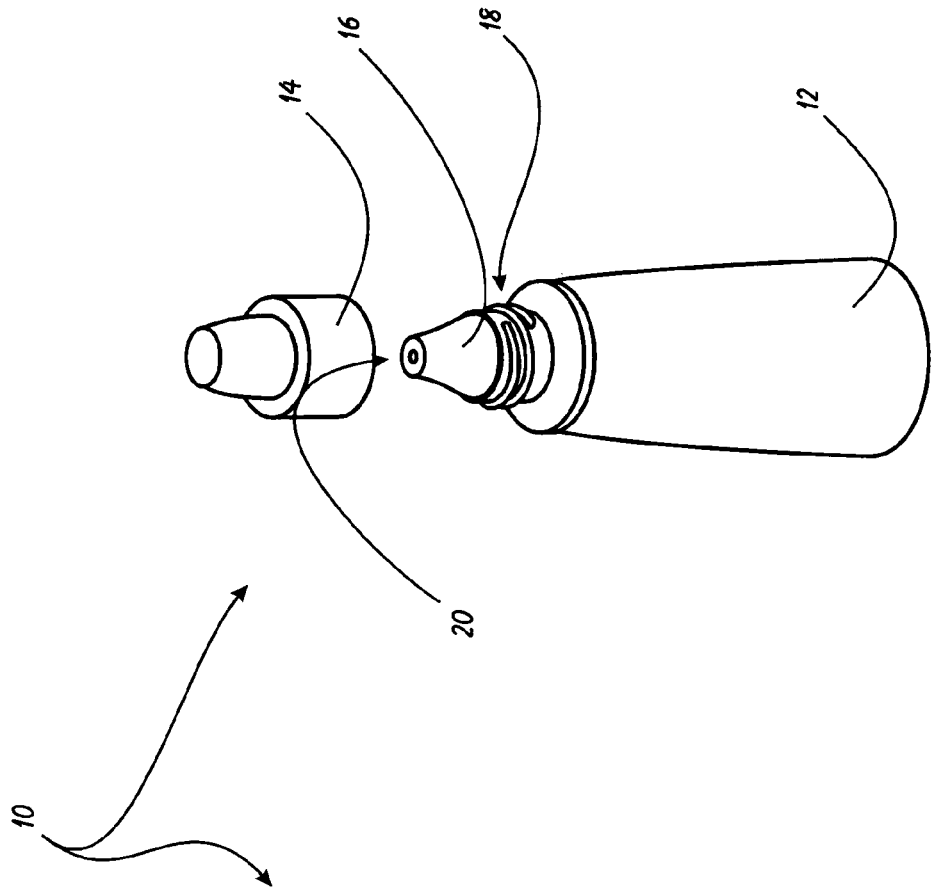
FIG. 2 is a partially exploded perspective view of the dispenser of FIG. 1.
Figure 1:
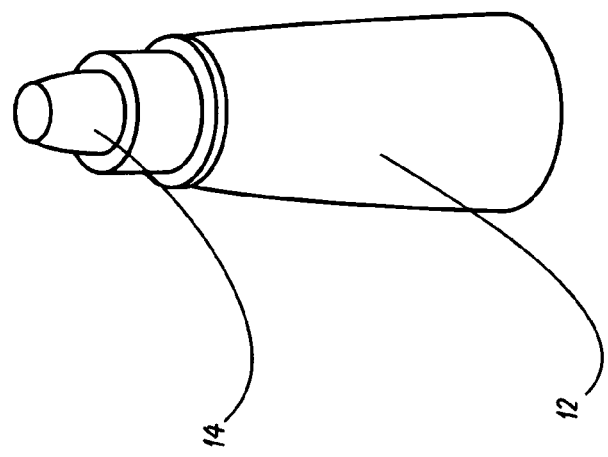
FIG. 1 is perspective view of a conventional disposable eyedrop dispenser.
Figure 3:
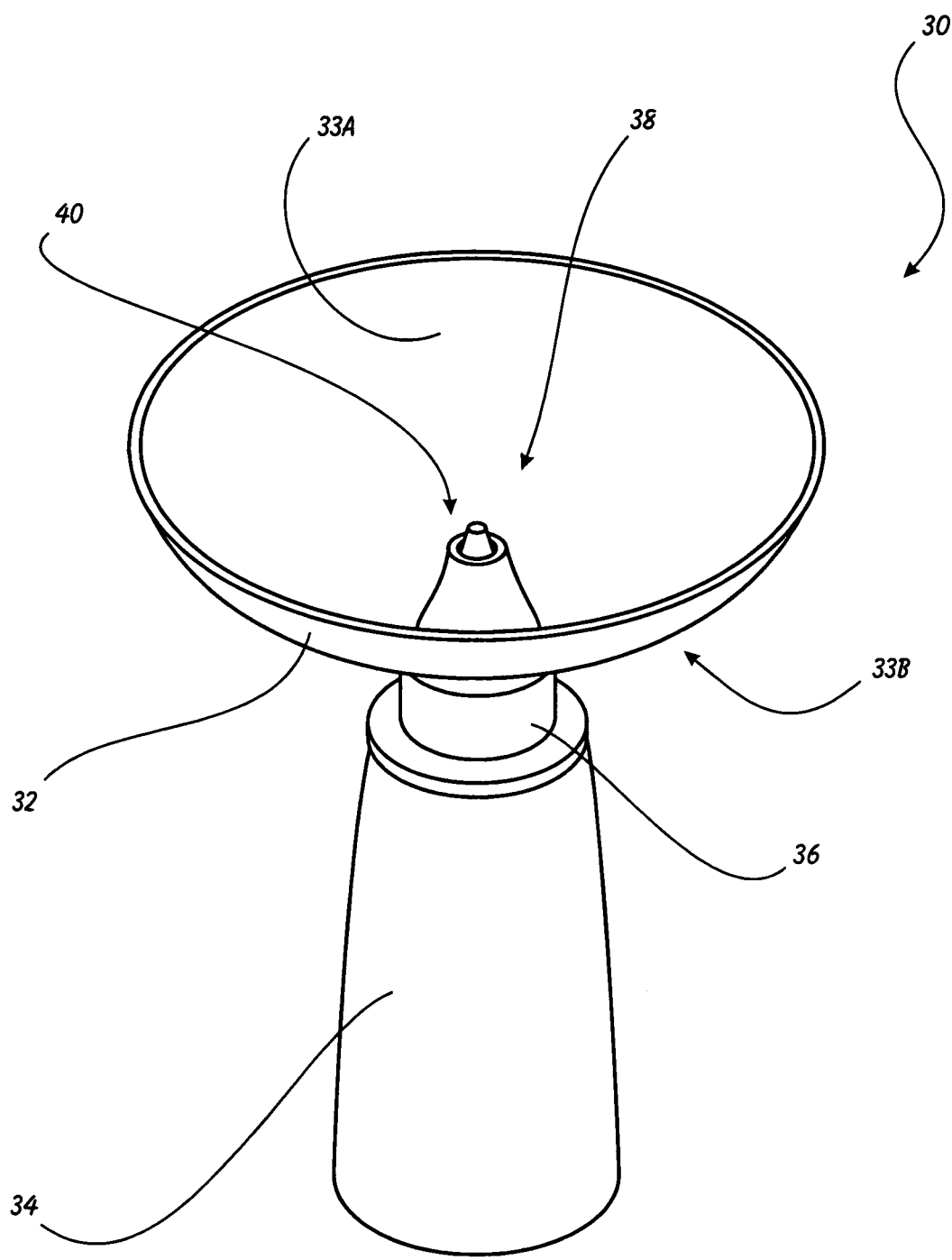
FIG. 3 is a perspective view of a preferred embodiment of the combination eye cup and drop dispenser of the present invention.

The present invention can best be understood by initial consideration of FIG. 3. FIG. 3 is a perspective view of a preferred embodiment of the combination eye cup and drop dispenser 30 of the present invention. The dispenser 30 has two main components, the bottle 34 and the eye cup 32. The eye cup 32 is rounded to form an inner concave side 33A and an outer convex side 33B.

Figure 4:
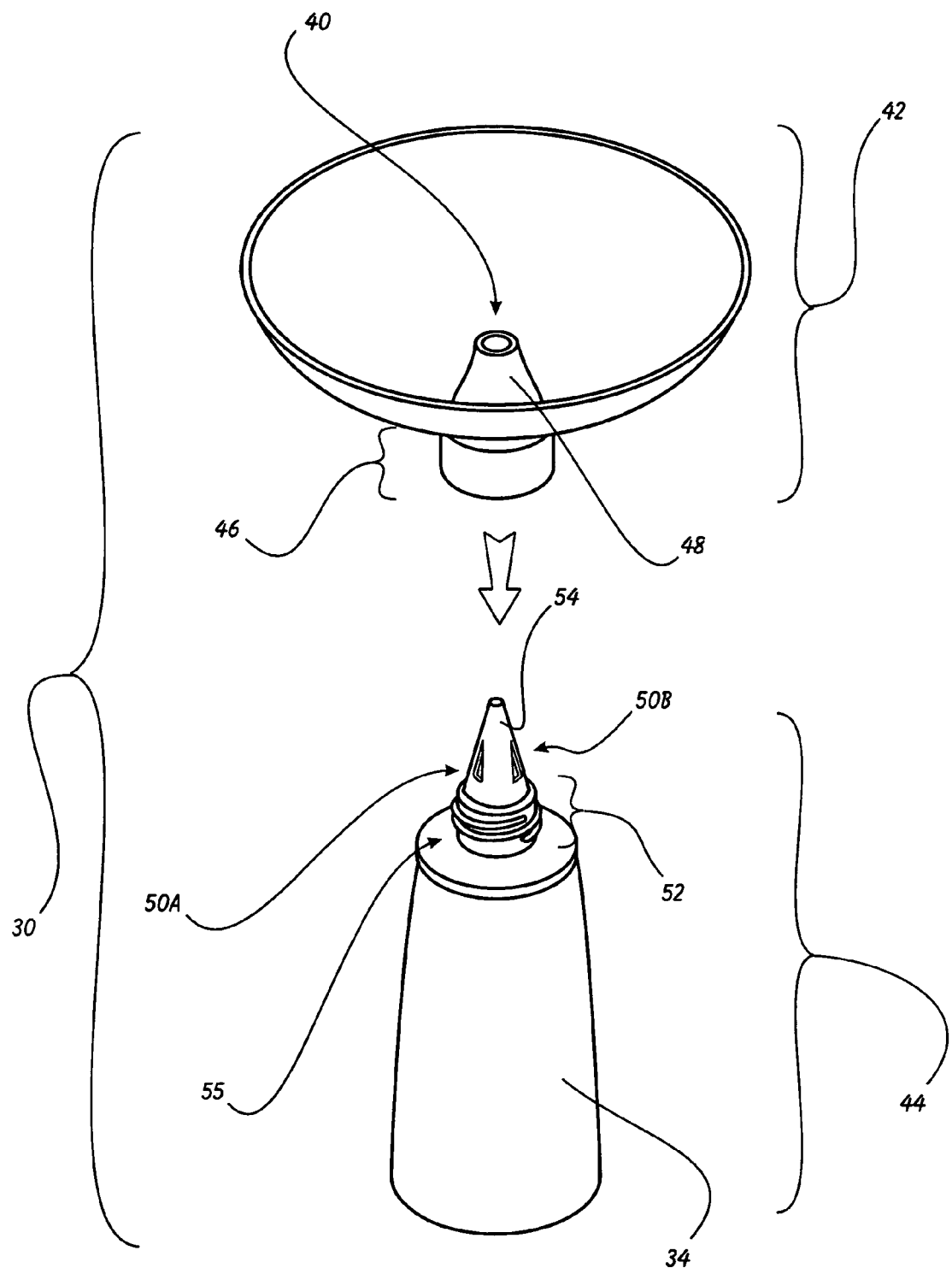
FIG. 4 is an exploded perspective view of the device of FIG. 3.

As is described more fully below, the unique benefit of this design is that the dispenser 30 integrates the cap, valve and eye cup into a single component or assembly. As a result, the user only needs to twist the eye cup 32 in order to open or close the valve. The nozzle valve 38 is located within the concave side 33A of the eye cup 32, and, when opened, allows eye drops to be dispensed through the orifice 40. The cap 36 is either integrated or attached to the eye cup 32. FIG. 4 provides additional detail of the design.

FIG. 4 is an exploded perspective view of the device 30 of FIG. 3. The eye cup cap 42, as shown, is both an eye cup and a cap for the bottle. The nozzle orifice 40 is within the concave portion of the cup. A neck portion 46 has internal threads (not shown here) for engagement with the external threads 52 on the bottle assembly 44. The nozzle portion 48 extends from the neck portion 46 to the nozzle orifice 40. The nozzle portion 48 defines a generally conical shape.

Figure 5:
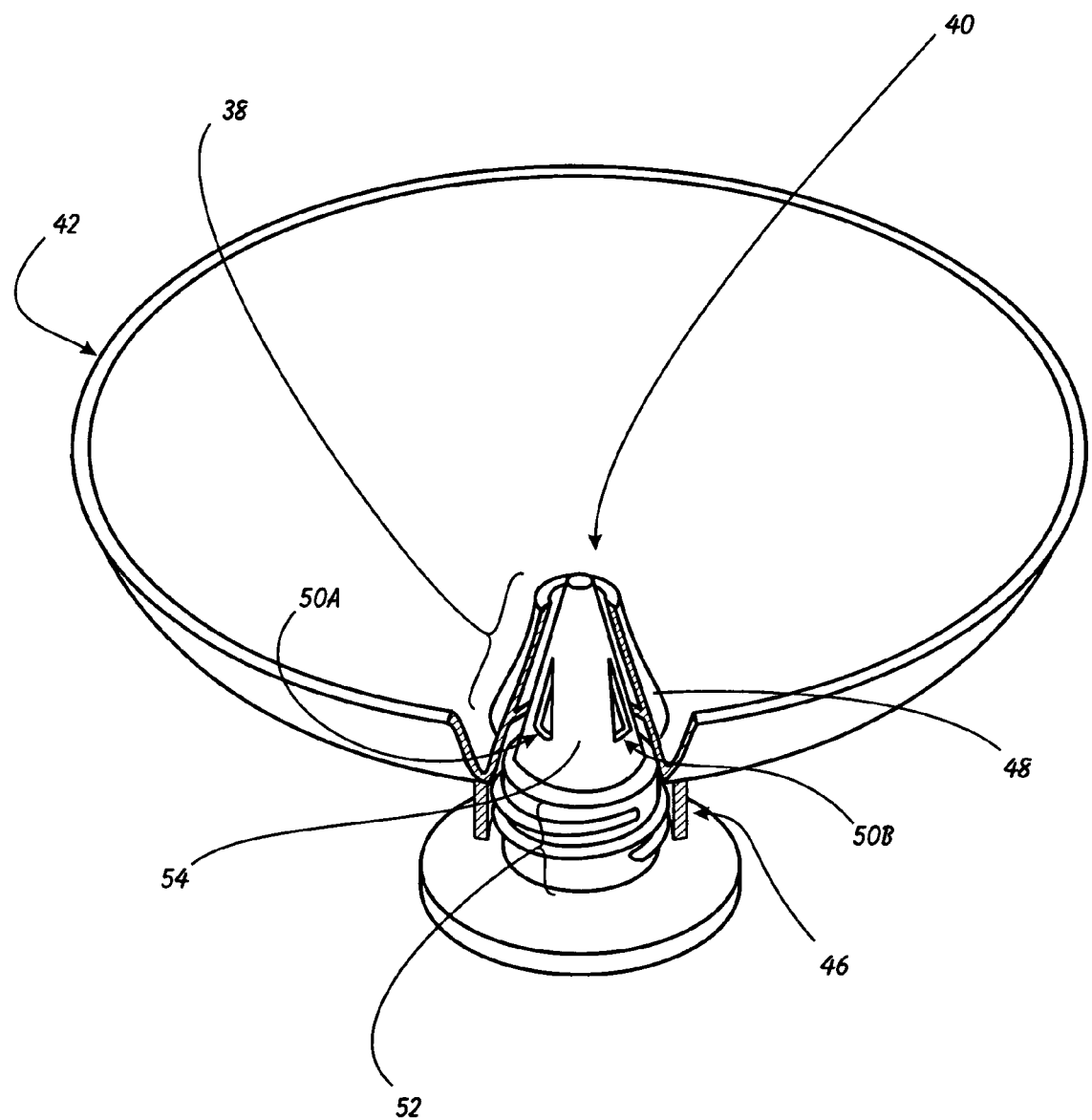
FIG. 5 is a partially cutaway perspective view of the eye cup cap and nozzle portion of the device of FIGS. 3 and 4.

The bottle assembly 44 comprises the bottle 34 that terminates at its upper end in the nozzle core section 54. The nozzle core section 54 has a generally conical shape and includes one or more bottle orifices (e.g. 50A, 50B) around its circumference. As discussed previously, the bottle assembly 44 has external threads 52 formed around the neck region 55 so that they will engage the internal threads formed within the neck portion 46 of the eye cup cap 42 to both seal the bottle contents and also to allow dispensing of the contents when desired. FIG. 5 provides additional detail regarding the operation of the device.

FIG. 5 is a partially cutaway perspective view of the eye cup cap 42 and nozzle portion 48 of the device of FIGS. 3 and 4. As is illustrated here, the neck portion 46 has engaged the external threads 52 of the bottle. The tip of the nozzle core section 54 is shown as protruding up beyond the upper edge of the nozzle orifice 40, but this is not necessarily the arrangement of the elements in all versions of the device.

The operation of the nozzle valve 38 is as follows: when the eye cup cap 42 is rotated (clockwise here), it will tighten down onto the bottle until the inner surface of the nozzle portion 48 is forced against the nozzle orifices 50A, 50B (and any others) until the orifices 50A, 50B are sealed.

When the eye cup cap 42 is rotated the opposite direction (counter-clockwise here), the orifices 50A, 50B are unsealed. Once the orifices 50A, 50B are unsealed, fluid will be allowed to pass between the inner surface of the nozzle portion 48 and the outer surface of the nozzle core section 54. Since the user will be inverting the bottle in order to place the drops into the eye, gravity will cause the fluid to exit towards the nozzle orifice 40 (rather than towards the threads 52). The eye cup cap 42, as with the Sbarra and Silver devices, allows the user to steady his or her hand while the drops are being dispensed into the user's eye through the nozzle orifice 40. When done, the user need simply tighten down the eye cup cap 42 (i.e. rotate it clockwise here) until the orifices 50A, 50B (and any others) are sealed. This simple, yet functional design provides a low cost of manufacturing and very simple operations.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A combination eye cup and drop dispenser, comprising:
an eye cup cap having a neck portion defined by internal threads, a cup portion, and a nozzle portion, the nozzle portion defined by a nozzle aperture and an inner nozzle surface, said eye cup cap formed as a single integrated piece consisting of said neck portion, said cup portion, and said nozzle portion;
a bottle assembly defined by a bottle and a nozzle core section, said nozzle core section and said eye cup cap neck portion cooperatively designed such that said nozzle core section is insertible within said neck portion to engage said internal threads, said nozzle core section is defined by a threaded portion having external threads integrally formed on said nozzle core section and said nozzle core section further defined by a tapered conical portion defined by one or more nozzle core apertures formed thereon, said nozzle core section terminating in a tip; and
whereby said eye cup cap internal threads directly engage said nozzle core section external threads and said eye cup cap can be rotated relative to said bottle assembly such that said inner nozzle surface seals each said nozzle core aperture, whereby said inner nozzle surface and said nozzle core section form a valve therebetween, said inner nozzle surface being in spaced relation to an outer surface of said nozzle core section when the valve is open, and the rotation of the eye cup cap relative to the bottle assembly tightening and loosening the engagement of the internal and external threads.

2. The dispenser of claim 1, wherein said bottle assembly further comprises:
said bottle terminating in a bottom closed first end and said nozzle core section at an opposing conically-shaped second end, said nozzle core section external threads formed on an outer surface for engagement with said eye cup cap internal threads.

3. The dispenser of claim 2, wherein said eye cup cap is further defined by said nozzle portion extending upwardly from said neck portion, said nozzle portion defining a generally conical shape, whereby said nozzle core section fits within said nozzle portion.

4. The dispenser of claim 3, wherein said eye cup cap cup portion is further defined by an internal concave side and an external convex side, said nozzle portion extending from said internal concave side.

5. The dispenser of claim 4, wherein said neck portion extends from said external convex side.

6. The dispenser of claim 4, wherein said eye cup cap cup portion extends from a perimeter area located in between said nozzle portion and said neck portion.

7. A fluid dispenser, comprising:
an eye cup cap having a generally conical nozzle portion extending upwardly from a convex eye cup section;
a bottle assembly defined by a bottle and a nozzle core section, said nozzle core section and said eye cup cap nozzle portion cooperatively designed such that said nozzle core section is insertible within said nozzle portion, said bottle assembly terminating in a closed first end and at a second opposing end at said nozzle core section; and
a nozzle valve formed by interaction between said conical nozzle portion and said nozzle core section such that rotation of said eye cup cap relative to said bottle assembly selectively opens said nozzle valve by rotating said eye cup cap relative to said bottle assembly until an inner surface of said conical nozzle portion is in spaced relation to the outer surface of said nozzle core section and one or more nozzle core orifices formed in said nozzle core section, and closes said nozzle valve by counterrotating said eye cup cap relative to said bottle assembly until said nozzle portion inner surface is pressed against said nozzle core section to seal said nozzle core orifices, said rotation and counterrotation said eye cup cap relative to said bottle assembly involves tightening and loosening engagement of threads formed cooperatively on said nozzle core section and said eye cup cap.

8. The dispenser of claim 7, wherein said convex eye cup section of said eye cup cap is further defined by an internal concave side and an external convex side and said nozzle portion protrudes upwardly from said internal concave side.

9. The dispenser of claim 8, wherein said bottle assembly further comprises:

said bottle terminating in a closed first end and said nozzle core section at an opposing second end, said nozzle core section having a generally conical shape and further defined by external threads formed on an outer surface of a neck region adjacent to said nozzle core section for engagement with eye cup cap internal threads formed on an inner surface of neck portion of said eye cup cap, said neck portion extending downwardly from said external convex side.

10. The dispenser of claim 9, wherein said nozzle portion defines a generally conical shape, whereby said nozzle core section fits within said nozzle portion when said external threads engage said internal threads.

11. The dispenser of claim 10, wherein said eye cup cap is defined by a cap having said neck portion at a bottom end and said nozzle portion at an opposing end, said nozzle portion terminating in a nozzle orifice.

12. The dispenser of claim 11, wherein said convex eye cup section extends from a perimeter area between said nozzle portion and said neck portion.

13. The dispenser of claim 12, wherein said nozzle core section has at least two orifices formed therethrough, said nozzle core section and said nozzle portion cooperatively designed such that said nozzle portion can engage to seal said at least two nozzle core orifices by rotating said eye cup cap relative to said bottle assembly.

14. A fluid dispenser, comprising:

an eye cup cap defined by a generally conical nozzle portion terminating in a eye cup cap nozzle portion orifice, said eye cup cap defined by a cup portion having an internal concave side and an external convex side and said nozzle portion protrudes upwardly from said internal concave side, said nozzle portion and said cup portion integrated as a single item;

a bottle assembly defined by a bottle having a closed first end and a nozzle core section at an opposing second end, said nozzle core section and said eye cup cap nozzle portion cooperatively designed such that said nozzle core section is insertible within said nozzle portion, said nozzle core section having at least two orifices formed therethrough to provide access to an internal volume formed in said bottle; and a nozzle valve formed by interaction between said conical nozzle portion and said nozzle core section such that rotation of said eye cup cap relative to said bottle assembly selectively opens said nozzle valve by rotating said eye cup cap relative to said bottle assembly until an inner surface of said conical nozzle portion is in spaced relation to the outer surface of said nozzle core section and two or more nozzle core orifices formed in said nozzle core section, and closes said nozzle valve by counterrotating said eye cup cap relative to said bottle assembly until said nozzle portion inner surface is pressed against said nozzle core section to seal said nozzle core orifices.

\* \* \* \* \*